United States Patent [19]
Nonomura et al.

[11] Patent Number: 5,597,400
[45] Date of Patent: Jan. 28, 1997

[54] METHODS AND COMPOSITIONS FOR ENHANCING CARBON FIXATION IN PLANTS

[76] Inventors: Arthur M. Nonomura, 145 E. Estero La., Litchfield Park, Ariz. 85340; Andrew A. Benson, 6044 Folsom Dr., La Jolla, Calif. 92037

[21] Appl. No.: 351,348

[22] PCT Filed: Jun. 14, 1993

[86] PCT No.: PCT/US93/05676

§ 371 Date: Feb. 24, 1995

§ 102(e) Date: Feb. 24, 1995

[87] PCT Pub. No.: WO94/00009

PCT Pub. Date: Jan. 6, 1994

Related U.S. Application Data

[63] Continuation-in-part of Ser. No. 901,366, Jun. 19, 1992, abandoned.

[51] Int. Cl.[6] ............................. A01N 31/02; C05C 9/00
[52] U.S. Cl. ...................... 71/28; 71/29; 71/30; 504/118; 504/148; 504/353
[58] Field of Search .......................... 71/28–30; 504/718, 504/148, 353

[56] References Cited

U.S. PATENT DOCUMENTS

| | | | |
|---|---|---|---|
| 3,472,647 | 10/1969 | Miller | 71/122 |
| 3,764,294 | 10/1973 | Miller | 47/59 |
| 3,915,686 | 10/1975 | Miller | 71/79 |
| 3,918,952 | 11/1975 | Neumiller | 71/28 |
| 4,033,745 | 7/1977 | Moore | 71/28 |
| 4,190,428 | 2/1980 | Colton et al. | 71/29 |
| 4,409,015 | 10/1983 | Grace, Jr. | 71/28 |
| 4,576,626 | 3/1986 | Bauer et al. | 71/28 |
| 4,863,506 | 9/1989 | Young | 71/113 |
| 5,071,466 | 12/1991 | Kuraishi et al. | 71/88 |

FOREIGN PATENT DOCUMENTS 1046886A  11/1990  China.

OTHER PUBLICATIONS

Pavlova and Kudrev (1986) *Dolk. Bolg. Akad. Nauk.* 39:101–103 no month, Influence Of Leaf Feeding On [14]C–Proline Uptake By Forming Wheat Grain.

Barel and Black (1979) *Agron. J.* 71:21–24 no month, Foliar Application of P. II. Yield Responses of Corn and Soybeans Sprayed with Various Condensed Phosphates and P–N Compounds in Greenhouse and Field Experiments.

Nonomura and Benson (1992) *PNAS* 89:9794–9798, The path of carbon in photosynthesis: Improved crop yields with methanol no month.

Harder et al. (1973) *J. Gen. Microbiol.* 78:155–161, Methanol Assimilation by Hyphomicrobium sp.

Hungarian Patent Abstr. T45468 (Jul. 28, 1988).

USSR Patent Abstr. 84–3794472 (Oct. 1, 1984).

(List continued on next page.)

*Primary Examiner*—Ferris Lander
*Attorney, Agent, or Firm*—Townsend and Townsend and Crew LLP

[57] ABSTRACT

Plant growth stimulants containing compounds which increase intracellular carbon dioxide as the main active component and optionally supplemented with specific nutrients have been found to enhance productivity of plants. Exemplary compounds include lower alcohols, such as methanol, ethanol, propanol and butanol, and amino acids, such as glycine, glutamate, and aspartate. Such growth stimulation appears to result, in part, from inhibition of stress induced photorespiration according to a previously unrecognized photosynthetic pathway. Exposure of the plants to sunlight or other sufficient illumination following treatment with the compositions results in enhanced fixation of carbon dioxide and turgor. Stimulant compositions may comprise from 5% to 50% by volume aqueous solutions of methanol or 0.1% to 10% by weight amino acids and are preferably applied by foliar spraying of plants and plant shoots.

13 Claims, 2 Drawing Sheets

OTHER PUBLICATIONS

Schuler and Paulsen (1988) *J. Plant Nutr.* 11:217–233, Nitrogen Nutrition And Growth Regulator Effects Of Oxamide on Wheat And Soybean.

Benson et al. (1951) *J. Am. Chem. Soc.* 73:2971, Identification Of Riboluse In $CHO_2$ Photosynthesis Products no month.

Quayle et al. (1954) *J. Am. Chem. Soc.* 76:3610, Enzymatic Carboxylation Of Ribulose Diphosphate no month.

Cossins (1964) *Canadian J. Biochem.* 42:1793–1802, the Utilization Of Carbon–1 Compounds By Plants no month.

Cooney et al. (1972) *Adv. Appl. Microbiol.* 15:337, Microbial Utilization of Methanol no month.

5,597,400

1

METHODS AND COMPOSITIONS FOR ENHANCING CARBON FIXATION IN PLANTS

This application is a national stage filing of PCT/US93/05676, filed Jun. 14, 1993 which is a continuation-in-part of U.S. application Ser. No. 07/901,366, filed Jun. 19, 1992, now abandoned.

BACKGROUND OF THE INVENTION

1. Field of the Invention

The present invention relates generally to methods and compositions for stimulating and maintaining enhanced growth in plants. More particularly, the present invention relates to plant growth formulations which contain methanol, methanol metabolites and/or amino acids, which compositions are able to increase turgor pressure and enhance carbon fixation in plants.

Photosynthesis is the process by which photosynthetic plants utilize solar energy to build carbohydrates and other organic molecules from carbon dioxide and water. The conversion of carbon dioxide to such organic molecules is generally referred to as carbon fixation and, in most plants, occurs by the reductive pentose phosphate cycle, usually referred to as the $C_3$ cycle. The $C_3$ cycle involves the carboxylation of ribulose diphosphate (RuDP) with carbon dioxide to produce hexoses and other organic molecules.

Fertilizers for higher plants generally include nitrogen, phosphorus, and potassium, which are referred to as primary nutrients or macronutrients. Fertilizers often further include certain secondary nutrients, such as iron, sulfur, calcium, and magnesium, as well as various minerals and micronutrients. Heretofore, little attention has been paid to providing fertilizers which act directly to enhance carbon fixation in higher plants. Conventional fertilizer formulations have generally been directed at the delivery of the recognized primary, secondary, and micronutrients, but have usually not included a carbon source and in particular have not included a carbon source intended to enhance carbon fixation by the $C_3$ cycle or otherwise.

For these reasons, it would be desirable to provide improved methods and formulations for promoting plant growth by enhancing the rate of carbon fixation within the plant. It would be particularly desirable if such methods and compositions were effective with most or all higher plants, more particularly including those plants which fix carbon via the $C_3$ pathway. The present invention should further provide convenient methods for applying the compositions, such as applying the compositions as a foliar spray, and should preferably result in increased plant turgidity. Additionally, it would be desirable if the methods and compositions of the present invention could promote rapid growth and maturing of the treated plant, increase sugar content in the plant, reduce the watering requirement of the plant, and enhance environmental tolerance of the plant.

2. Description of the Background Art

Study of the path of carbon in photosynthesis four decades ago (A. A. Benson (1951), "Identification of Ribulose in $C^{14}O_2$ Photosynthesis Products" J. Am. Chem. Soc. 73:2971; J. R. Quayle et al. (1954), "Enzymatic Carboxylation of Ribulose Diphosphate" J. Am. Chem. Soc. 76:3610) revealed the nature of the carbon dioxide fixation process in plants. The metabolism of one-carbon compounds other than carbon dioxide had been examined, and methanol was found to be utilized by algal strains of Chlorella and Scenedesmus for sugar and amino acid production as rapidly as is carbon dioxide. Since both types of early experiments were performed with substrate on a tracer scale, it was neither clear that the rates were comparable nor what the pathway for methanol conversion to sucrose involved. A subsequent publication on the subject (E. A. Cossins (1964), "The Utilization of Carbon-1 Compounds by Plants" Canadian. J. Biochem. 42:1793) reported that plants metabolize methanol to carbon dioxide, glycerate, serine, methionine, and other sugar or structural precursors rapidly. The conclusion that methanol is readily oxidized to formaldehyde and converted to fructose-6-phosphate has been reported in bacteria (C. L. Cooney and D. W. Levine (1972), "Microbial Utilization of Methanol" Adv. Appl. Microbiol. 15:337) and fungi (W. Harder et al. (1973), "Methanol Assimilation by Hyphomicrobium sp." J. Gen. Microbiol. 78:155). Based on these studies of microorganisms it was concluded that formaldehyde condenses with pentose-5-phosphate to yield allulose-6-phosphate which epimerizes to fructose-6-phosphate.

Methanol and other alcohols have been included in certain prior fertilizer formulations for various purposes. U.S. Pat. No. 3,918,952, discloses the incorporation of 1–15 parts by volume lower alcohol in clear liquid fertilizers as stability enhancers. U.S. Pat. No. 4,033,745, discloses the incorporation of 0.05% to 1% alcohol in liquid fertilizers as a stability enhancer. U.S. Pat. Nos. 4,409,015 and 4,576,626 describe the addition of alcohols to fertilizers to enhance solubilization of phospholipids. See also Hungarian patent abstract T45468 and USSR patent abstract 84-3794472, which describes the incorporation of methanol into fertilizers at unspecified concentrations.

British patent application 2 185 472 A describes foliar plant feeding compositions which comprise from 2% to 4% by weight of protein hydrosylate including amino acids, polypeptides, and oligopeptides. Particular amino acids are not identified. The application of oxamide ($H_2N$—CO—CO—$NH_2$) in foliar sprays to wheat and soybean as a slow-release of nitrogen source is described in Schuler and Paulsen (1988) J. Plant Nutr. 11:217–233. The foliar application of radiolabelled proline to wheat is described in Pavlova and Kudrev (1986) Dolk. Bolg. Akad. Nauk. 39:101–103. Barel and Black (1979) Agron. J. 71:21–24 describes foliar fertilizers incorporating polyphosphate compounds combined with a surfactant (0.1% Tween® 80). Chinese patent publication 1046886A describes plant leaf fertilizers including amino acids. U.S. Pat. No. 4,863,506, describes the incorporation of L-(d)-lactic acid in foliar sprays where the lactic acid is alleged to act as a growth regulator.

A portion of the experimental section presented in this application was published in Nonomura and Benson (1992) Proc. of the Natl. Acad. of Sci. USA 89:9794–9798. This publication occurred prior to the filing date of the patent application Ser. No. 07/901,366.

SUMMARY OF THE INVENTION

A method for promoting the growth of plants, particularly green plants and other photosynthetic organisms, comprises foliar or other application to the plant of a compound selected to increase intracellular carbon dioxide levels in amounts sufficient to inhibit photorespiration, particularly while the plant is exposed to conditions which otherwise induce photorespiration, such as high light intensity, heat, water stress, nutrient stress, and the like. Compounds which produce such levels of intracellular carbon dioxide may be selected based on the metabolic pathway set forth in FIG. 1, and include lower alcohols, particularly including methanol, but also including ethanol, as well as amino acids, particularly including glycine, glutamate, glutamine, alanine and aspartate. Such intracellular carbon dioxide enhancing compounds will typically be applied to the plants in the presence of a phosphate compound, and optionally other known plant nutrients, and may have other growth promoting activities in addition to carbon dioxide enhancement. Frequently, it will be desirable to also include a surfactant in the compositions in order to enhance leaf wetting and penetration of the compound and other components. Preferably, the compound will be applied as a foliar spray while the plant is exposed to a relatively high light intensity, typically a least about 1000 µEIN/m²/sec.

In a particular aspect of the present invention, growth of plants is promoted by applying a growth promoting composition comprising an amount of a lower alcohol, particularly methanol or methanol plant metabolite, sufficient to increase plant turgidity (turgor pressure) and enhance carbon fixation within the plant. The composition comprises an aqueous solution of the methanol or methanol plant metabolite, usually being methanol at 5% to 50% by volume. The plant growth promoting compositions optionally include a number of other components and nutrients, such as glycine, and glycerophosphate (which enhance carbon dioxide fixation under low light conditions), a nitrogen source, a phosphorus source, secondary nutrients, micronutrients, and the like. The composition will generally also include a surfactant to facilitate wetting and penetration of the methanol, methanol metabolite, and other components, into the plant tissue.

The compositions of the present invention are usually applied to a plant as a foliar spray, with direct application to portions of the plant exposed to sunlight being preferred. The methods of the present invention are most effective with plants which fix carbon via the $C_3$ pathway, and best results are obtained exposing the plant to sunlight or other illumination (typically having an intensity of at least 1000 µEin/m²/sec.) for a period of time sufficient for photosynthetic metabolism of the methanol or methanol plant metabolite to take place, usually continuing such illumination for at least 2 hours, and preferably 4 hours after the initial composition application. In this way, photosynthetic (metabolic) conversion of the methanol and consequent alteration of the photosynthetic apparatus can be efficiently achieved. The use of glycine and/or glycine and glycerophosphate in the plant growth promotant formulation will enhance photosynthesis and passage of the methanol and its metabolites through biochemical pathways with efficiency and safe uptake under lower illumination conditions, such as with plants located indoors.

Plant growth promoting compositions of the present invention will also comprise an aqueous solution of an amino acid, a phosphate compound, and a surfactant, where the amino acid is selected to increase intracellular carbon dioxide levels when applied foliarly to the plant. The amino acid compound will be present in the composition in a concentration effective to inhibit photorespiration and enhance plant growth. The phosphate will be provided in order to provide sufficient phosphorous to support energy reactions required for such plant growth. The surfactant is present in an amount sufficient to enhance penetration of the remaining components of the composition into plant cells, particularly when the compositions are applied to plants having waxy leaves which otherwise might inhibit penetration. Preferred amino acids include glycine, glutamate, glutamine, alanine and aspartate, which are present in the compositions at concentrations from 0.1% to 10% by weight.

It has been found that use of the plant growth promotant compositions of the present invention can result in increased growth in treated plants by from 20% to 100%, or more, when compared to the use of similar fertilizer formulations without the methanol or methanol metabolite component. In addition to such enhanced growth, the fertilizers and methods of the present invention will often increase plant turgidity and sugar content, provide for more rapid plant maturation, reduce water requirements, and enhance tolerance to other environmental conditions by the treated plants. It is believed that the methanol and/or amino acid component itself contributes only minor amounts of carbon to the plant and that the compound acts primarily to alter and promote the plant's photosynthesis to provide a great increase in carbon fixation and growth.

DESCRIPTION OF SPECIFIC EMBODIMENTS

Figure 1:
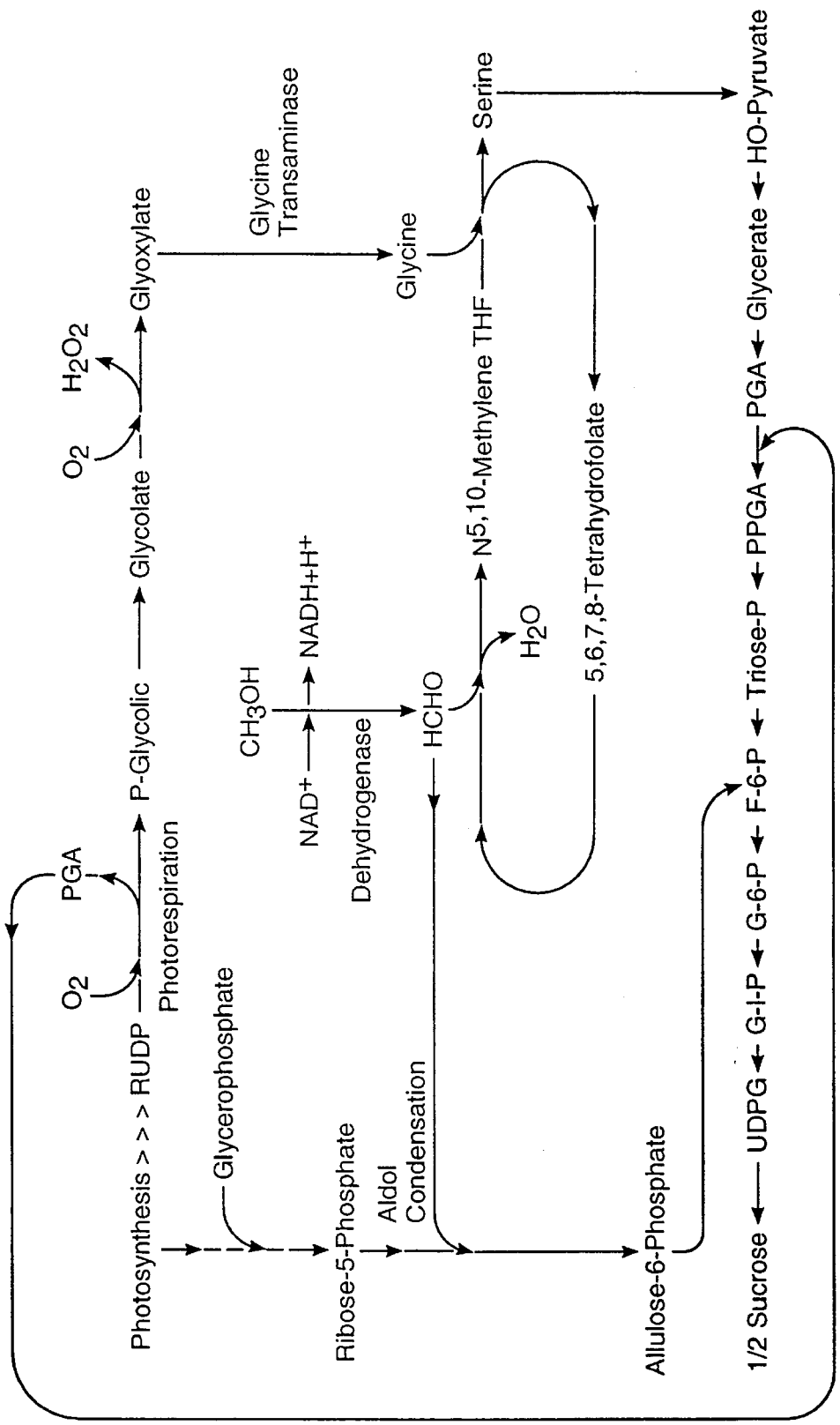
FIG. 1 illustrates a metabolic pathway for methanol and amino acid utilization and consequent growth enhancement in plants.
Figure 2:
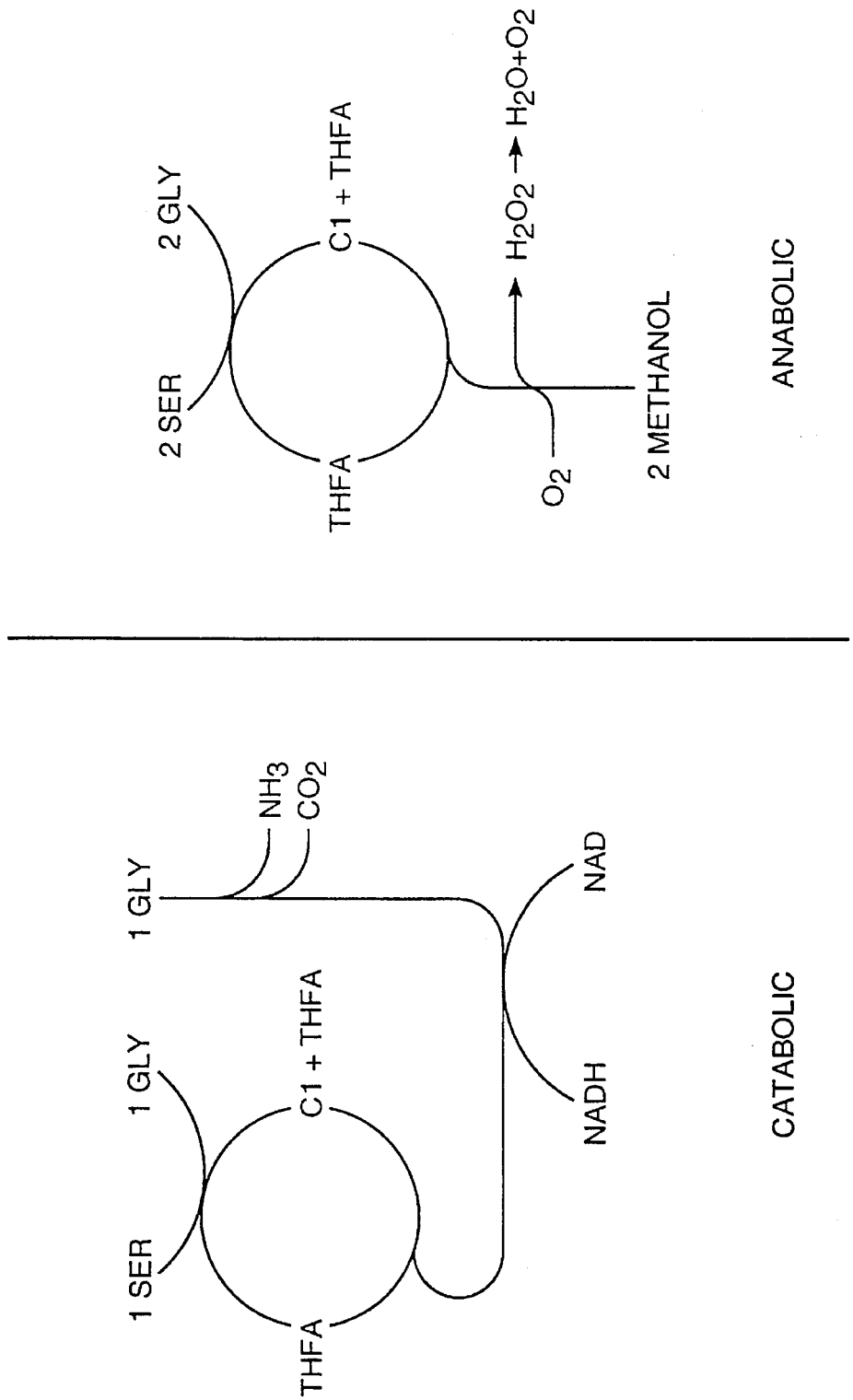
FIG. 2 illustrates anabolic and catabolic pathways for glycine utilization in plants. Normally for photorespiration, two molecules of glycine yield one molecule of serine plus carbon dioxide, ammonia and cofactors. Alteration of the pathway by addition of methanol would yield two molecules of serine per entry of two molecules of glycine. Doubling the quantity of serine could lead to twice the sucrose being produced, but the requirement for glycine necessitates high rates of photorespiration.

The present invention provides novel and effective compositions and methods for promoting the growth of green and other photosynthetic plants, particularly higher plants. The method relies on applying compounds such as methanol, methanol metabolites and amino acids (as defined hereinafter) as a foliar spray to the plant and its leaves, where the compound is selected to increase intracellular carbon dioxide levels in an amount sufficient to inhibit photo respiration within the plant cells and thus enhance plant growth. The compounds having this capability may be identified by reference to a previously unrecognized pathway as set forth in FIG. 1. Alternatively, useful compounds can be identified by reference to the decarboxylation pathways set forth in FIG. 2. The pathway of FIG. 1 appears to involve the photosynthetic apparatus in the sense that sunlight or other strong illumination is required for efficient utilization of the methanol, methanol plant metabolites and amino acids in the enhanced production of sucrose and structural components from carbon dioxide. It is presently believed that the essential aspects of the sucrose synthesis pathway are as illustrated in FIG. 1, although it is to be understood that the effectiveness of the present invention does not depend on the accuracy or completeness of the particular representation. The representation is useful, however, in that it helps to provide an understanding of the variations of the procedures of the present invention and the parameters of light, humidity, and temperature which affect how it can be practiced.

The methods and compositions of the present invention are effective with virtually all photosynthetic plant species having leaves or other surfaces capable of receiving foliar sprays, particularly higher plants which fix carbon dioxide via the $C_3$ pathway, and may also find more limited use with plants which fix carbon via the $C_4$ and CAM pathways. "Higher" plants include all plant species having true stems, roots, and leaves, thus excluding lower plants, e.g. yeasts and molds. Suitable $C_3$ plants which may benefit from fertilization according to the present invention include crop plants, such as rice, peanuts, barley, broccoli, cauliflower, mint, grapes, potato, eggplant, zucchini, squash, cucumber, bean, lettuce, chard, sugar beet, radish, kale, tobacco, alfalfa, oats, soybean, turnip, parsnip, spinach, parsley, and the like; flowering plants, such as rose, coleus, chrysanthemum, poppy, African violets, bougainvillea, oleander, hibiscus, gardenia, jasmine, camellia, marigold, daisy, stock, vinca, gerbera, carnation, cyclamen, peony, shooting star, bird-of-paradise, forget-me-not, and the like; fruit trees, such as apple, plum, peach, cherry, citrus, and the like; and forest trees, such as pine, redwood, cypress, juniper, elm, birch, palm, and the like. This list is intended to be exemplary and not intended to be exclusive.

The methods and compositions of the present invention may be used to promote growth in tissues of either juvenile or mature plants. Generally, however, it is desirable that the plants include at least two true leaves beyond the cotyledon or cotyledon pair (i.e. the "seed leaves"). Improved growth occurs as a result of several pathways for the metabolism of methanol in which oxidation immediately generates carbon dioxide which will reduce photorespiration. With high rates of photorespiration, the path of carbon is redirected in the presence of methanol to combine $C_1$ THFA and glycine to produce serine, in combination with the persisting effects of methanol metabolites, notably formaldehyde, on the relative rates of some of the enzyme-catalyzed processes of the photosynthetic structures of the plant. In addition to such enhanced growth, treatment of plants with the compositions of the present invention results in an enhanced turgidity.

Turgor, the distension of the plant cell wall and membranes by increase of cellular fluid content, is increased with synthesis of sugar. Turgidity, being the opposite of wilt, is a positive symptom of plant vigor. High levels of turgor pressure distend guard cells, thereby increasing the stomatal opening and allowing improved assimilation of carbon dioxide. Enhanced turgidity therefore translates to improved photosynthesis in the presence of light. Such enhanced turgidity generally results in a lessened water requirement and appears to also increase tolerance of the treated plants to environmental extremes, i.e. heat, cold, drought water stress, low humidity, high light intensity and the like.

The plant growth promoting compositions of the present invention will comprise an aqueous solution of methanol, a methanol plant metabolite and/or amino acid(s) present in an amount sufficient to increase intracellular carbon dioxide levels, inhibit photorespiration, and enhance carbon fixation and turgidity in a treated plant. The optimum amounts or concentrations of the active compound metabolite will vary depending on the plant species or variety being treated, the time of day, environmental factor(s), and the like.

For methanol, the concentration will generally be from 5% to 100%, usually being from 5% to 50% by volume, and more usually being from 10% to 30% by volume. Suitable methanol metabolites include those products of methanol which are apparent from the pathway of FIG. 1, particularly including formaldehyde and formic acid (and neutral analogs such as methyl formate). Such volume percentages are based on the total volume of the growth promotant composition.

For amino acids, the concentration will generally be from 0.1% to 10% by weight, usually being from 1% to 5% by weight. Suitable amino acids include all or most natural amino acids, and will particularly include those amino acids which readily penetrate into plant cells upon foliar application and which provide the desired carbon dioxide production. Preferred amino acids include glycine, glutamate, glutamine, alanine and aspartate, with glycine being particularly preferred as a precursor for methyl tetrahydrofolate ($C_1$ THFA), a formaldehyde donor.

While the growth promotant compositions of the present invention may consist essentially of the aqueous solutions of methanol, methanol plant metabolite and/or amino acids, as described above, they will usually contain other ingredients and components which improve performance in various ways. For example, the compositions will usually contain a surfactant present in an amount sufficient to promote leaf wetting and penetration of the methanol, methanol metabolite, and optionally other components, when the composition is applied to the plant as a foliar spray. Suitable surfactants include anionic and zwitterionic detergents, such as Teepol™ HB7, Tween™, nonylphenoxyhydroxy polyoxyethylene and isopropanol, Johnson's baby shampoo, and the like.

Compositions comprising methanol according to the present invention will preferably also contain components which enhance the production of sucrose via the alternate carbon fixation pathway of FIG. 1. Such components include the photorespiratory metabolites illustrated in FIG. 1, including glycolate, glyoxylate, glycine, serine, folate, peroxides, and the like. Other components which enhance such production include soluble salts of glycerophosphoric acid, such as disodium glycerophosphate, calcium glycerophosphate, L-glycerol 3-phosphate, phosphate esters of photosynthates, and the like.

Compositions comprising amino acids will also preferably contain a phosphate source, preferably a glycerophosphate or trimethyl phosphate present at from 0.1 weight percent to 5 weight percent, more preferably from 0.2 weight percent to 2 weight percent, in order to provide sufficient phosphorus to support the energy requirements of the enhanced growth provided by the composition of the present invention.

In addition to the above, both the methanol and the amino acid compositions of the present invention will often include one or more conventional fertilizer constituents, such as a nitrogen source, for example low biuret (LB) urea, nitric acid, sodium nitrate, or other nitrogen salts; a phosphorus source, such as phosphate salts, trimethylphosphate, phosphoric acid, organophosphates superphosphate, potassium pyrophosphate and the like; and a potassium source, such as potassium chloride, potassium sulfate, potassium nitrate, potassium acetate and the like. Compositions may further comprise secondary nutrients, such as sources of sulfur, calcium, and magnesium, as well as micronutrients, such as iron, boron, cobalt, copper, manganese, molybdenum, zinc, and the like. Incorporation of such primary, secondary, and micronutrients into liquid fertilizer formulations, is well described in the patent and technical literature. Other conventional fertilizer constituents which may be added to the compositions of the present invention include amino acids, peptides, vitamins, other biological metabolites of photosynthesis and photorespiration, insecticides, herbicides, fungicides, nematicides, antibiotics, plant growth regulators, nucleic acids, and the like.

Exemplary methanol plant growth promoting formulations according to the present invention for field (outdoor) use with very high light intensities and indoor (low light intensity) use are as follows.

Exemplary Methanol Formulations

| Constituent | Broad Concentration | Preferred Concentration |
|---|---|---|
| 1. Field Formulation | | |
| Methanol | 10% to 50% | 20% |
| Glycine | 0 g/l to 5 g/l | 1 g/l |
| LB Urea | 1 g/l to 55 g/l | 3 g/l |
| FeEDTA | 0.01 g/l to 0.1 g/l | 0.01 g/l |
| Triton ™ X-100 | 0.1 ml/l to 1 ml/l | 0.5 ml/l |
| Water | QID 1 liter | QID 1 liter |
| 2. Indoor Formulation | | |
| Methanol | 10% to 20% | 10% |
| Glycine | 1 g/l to 3 g/l | 1 g/l |
| Urea | 1 g/l to 6 g/l | 2 g/l |
| Urea phosphate | 0.1 g/l to 1 g/l | 1 g/l |
| FeEDTA | 0.01 g/l to 0.05 g/l | 0.01 g/l |
| Disodium glycerophosphate | 1 g/l to 10 g/l | 3 g/l |
| Triton ™ X-100 | 0.1 ml/l to 1 ml/l | 0.5 ml/l |
| Water | QID 1 liter | QID 1 liter |

The addition of glycerophosphate and glycine under low light conditions prevents foliar damage. Low light intensity is 100–150 μEin/m$^2$/sec. While direct sunlight is necessary for complete effectiveness of methanol and its metabolites for enhancing growth with the Exemplary Field Formulation, glycerophosphate and glycine prevent damage from methanol or its metabolites in treated plants exposed to obstructed sunlight or artificial light. The difference between field and indoor formulations is also based on the high temperatures caused by high light intensity. The lower indoor light intensities reduce the ability of the plant for photophosphorylation as well as its activation of its carbon dioxide fixation enzyme system, consequently, any additional phosphate and ATP provide useful assistance to the metabolic effort of the plant.

The methanol plant growth promoting compositions of the present invention may be prepared by obtaining a methanol in water solution having the appropriate concentration of methanol. The remaining ingredients are dissolved in the water, either before or after methanol addition, usually with stirring and optionally with heat addition. Care should be taken to store the formulations under conditions which do not result in precipitation of the constituents.

Exemplary amino acid formulations according to the present invention comprising glycine, glutamate, and aspartate, are as follows.

Exemplary Amino Acid Formulations

| Constituent | Concentration Ranges Broad | Preferred |
|---|---|---|
| Glycine | 1 g to 100 g | 50 g |
| Phosphate Buffer (e.g. citrate-phosphate) | pH 6.5–7 | pH 7 |
| Glycerophosphate | 1 g to 20 g | 10 g |
| Triton X-100 | 0.1 ml/l to 1 ml/l | 0.5 ml/l |
| Water | QID 1 liter | QID 1 liter |
| Glutamate | 1 g to 100 g | 20 g |
| Phosphate Buffer (e.g. TRIZMA succinate or oxalate) | pH 6.5–7 | pH 7 |
| Glycerophosphate | 1 g to 20 g | 1 g |
| Tetrapotassium pyrophosphate | 0 g to 2 g | 1 g |
| Triton X-100 | 0.1 ml/l to 1 ml/l | 0.5 ml/l |
| Water | QID 1 liter | QID 1 liter |
| Aspartate | 1 g to 100 g | 50 g |
| Phosphate Buffer (e.g. TRIZMA acetate) | pH 6.5–7 | pH 7 |
| Glycerophosphate | 1 g to 20 g | 2 g |
| Tetrapotassium pyrophosphate | 0 g to 2 g | 1 g |
| Triton X-100 | 0.1 ml/l to 1 ml/l | 0.5 ml/l |
| Water | QID 1 liter | QID 1 liter |

For both the methanol and the amino acid plant growth promoting formulations, it will be possible to prepare concentrated solutions which, upon appropriate dilution with water, will provide formulations suitable for direct application having the constituent concentrations within the ranges set forth above.

The amino acid plant growth promoting compositions of the present invention may be prepared by obtaining the amino acid, in liquid or dry form. For example, glycine may be obtained from W. R. Grace Company, Lexington, Mass., in bulk quantities, and may be dissolved in water to the appropriate concentration. The remaining constituents can then be added to the water solution, usually with stirring and optionally with heat addition. Care should be taken to store the formulations under conditions which do not result in precipitation of the constituents.

The plant growth promoting compositions of the present application are preferably applied as a foliar mist or spray. Usually, the fertilizer compositions will be sprayed from the top of the plant so that the aqueous solutions will land on the portions of the plant which are directly exposed to sunlight or other illumination source. Conventional spraying equipment can be used. For field plants, agricultural sprayers will be used. For indoor plants, hand-held sprayers may be used. A sufficient spray will be applied so that the leaf and other plant surfaces will be wet. In agricultural applications, the usage will generally be in the range from five gallons to 100 gallons per acre, usually being about 20 gallons per acre, with the 20% formulation. Usually, spraying with the fertilizer will be performed at a time between plant watering or irrigation.

It is preferred to apply the plant growth promoting compositions while the plants are exposed to direct sunlight or other suitable illumination. The plants should remain exposed to the sunlight or illumination for a period of time sufficient to permit plant turgidity to develop and allow for fixation of the applied carbon. Usually, the plants should remain exposed to sunlight or other illumination for at least two hours following fertilizer application, preferably for a period of at least four hours.

Plant illumination, either sunlight or artificial, should have an intensity sufficient to induce photorespiration and permit carbon fixation according to the pathway of FIG. 1. A minimum suitable illumination intensity is 100 μEin/m$^2$/sec, with direct sunlight normally providing much higher illumination. Of course, the inclusion of glycine with the glycerophosphate salt in the indoor formulations will enhance carbon fixation under low illumination intensity conditions, i.e. at or below 100 µEin/m²/sec. It is preferable, however, that the plant be exposed to at least two and preferably four hours of intense illumination following application of even the indoor formulations.

The following examples are offered by way of illustration, not by way of limitation.

EXPERIMENTAL

Materials and Methods

Field studies were initiated during the summer on irrigated farm fields in the desert southwest, Maricopa County, Arizona, United States of America. Preliminary tests were made in cotton fields where it was found that a single foliar treatment with 30% methanol and 0.1% surfactant resulted in production of larger leaves and taller plants than control plants (grown without methanol) after approximately two weeks. Further tests were made with savoy cabbages in the Fall; 20% methanol/0.1% surfactant applications resulted in improvements similar to cotton. After repeated applications of methanol, however, savoy cabbages showed symptoms of nitrogen deficiency. Thereafter, a minimal enhancement methanol medium was formulated containing (gm/L methanol): $NH_2CONH_2$ (15), FeHEEDTA (0.08) and Triton X-100 (2.5); added to water pH 6.5–7.0 to appropriate dilution.

Treatments of Savoy cabbages with methanol solutions in the Winter showed no appreciable stimulation of growth. In attempts to encourage growth, a methanol soluble major and minor nutrient medium was developed and included the following (gin/L): $NH_2CONH_2$ (10), $NH_2CONH_2.H_3PO_4$ (1), $CH_3COOH$ (4), $HOCH_2CH_2SO_3Na$ (1), $(CH_3COO)_2Mg.4H_2O$ (2), $Ca(NO_3)_2.4H_2O$ (1), FeEDTA (0.08); and minor nutrients (ppm) $(CH_3COO)_2Cu.H_2O$ (1), $(CH_3COO)_2Zn.2H_2O$ (1), $H_3BO_3$ (2), $(CH_3COO)_2Mn.4H_2O$ (1), $(CH_3COO)_2Co.4H_2O$ (0.1) and $12MoO_3.H_3PO_4$ (0.01). This major and minor nutrient medium did not result in perceptible differences in growth of most winter crops or shaded plants, but it was later utilized as a 10-fold concentrate to correct for nutrient deficiencies in citrus.

Supplementation of aqueous methanol solutions with 0.1% glutamate or 0.2% glycine increased growth of late winter and shaded plants. Glycine-methanol treatment of plants indoors under artificial illumination resulted in foliar damage 48–72 hours afterwards. Addition of 0.5% D,L-α-glycerophos-phate to glycine-enhanced methanol solutions was made to improve turgidity of plants under low light intensity (approximately 75–100 µEin/m²/sec) artificial illumination.

All treated and control soil borne plants were given sufficient fertilizers to maintain normal growth; container plants were supplemented with Osmocote 17-6-10 Plus Minors Plant Food for Potting Mixes comprising (percent composition) N (17), P (6), K (10), S (4), Ca (1.5), Mg (1), B (0.02), Cu (0.05), Cu (0.05), Fe (0.4), Mn (0.1), Mo (0.001), Zn (0.05); crop plants in open farm fields were supplemented with N, P, K and S farm grade fertilizers at rates consistent with agriculture for each variety.

Modes of Application

To prevent injury to foliage and to minimize frequency of application in fields, a concentration gradient of methanol in 5% increments was applied to crop plants to establish maximum dose response. Generally, methanol concentrations approximately 10% below the established toxicity level elicited a desired growth response. For example, a toxicity curve for methanol was established for cotton ranging from 1 percent to 50 percent methanol in pure water. At concentrations above 40 percent methanol, brown areas and leaf wilt were observed within 10 days. A concentration of 30 percent methanol in water did not damage cotton leaves; although, indentations in some cotton leaves retained 30% methanol for 24 hours or more and these areas became discolored and brittle. Treatment of cotton fields with 30% minimal enhancement methanol medium was repeated at weekly intervals in two passes. On the final application, 30 percent methanol without urea source was applied to stimulate maturation of cotton bolls.

Conventional agricultural equipment and machinery was utilized for application of methanol. For pilot scale foliar application on farm crops, 15 liter capacity SOLO backpack sprayers outfitted with Tee Jet 8003 flat-spray nozzles were utilized. Generally, application of 100% methanol soluble nutrient concentrates to tree trunks and stems was made with this backpack sprayer system.

Large scale field crops were sprayed with tractors equipped as follows: a tractor was mounted with jet stream-agitated saddle tanks, hydraulic vane pump, and six-row spray-boom with Tee Jet 8004 flat spray nozzle tips. Height and spacing of nozzles were set to spray directly over the tops of plants at the center of each row. Pressure and tractor speed was maintained to achieve a rate of application of 186 L/Hectare. As an example, a methanol solution for spraying cotton fields from a tractor follows: in 500 liter capacity tanks, 150 liters methanol with 0.25 liter of nonylphenoxy-hydroxypoly (oxyethylene) isopropanol and 1 gm FeHEEDTA was added to 350 liters pH 6.5 water containing 1.5 kg low biuret (LB) urea and 0.25 kg calcium nitrate with continuous agitation and the solution was pumped through the tractor mounted spray device for foliar coverage. Treatment of crops with the methanol solution was repeated between irrigation sets as necessary. Methanol-treated plants were otherwise treated the same as the remainder of the crop until maturation.

In greenhouses, methanol or nutrients in water were injected into the overhead mist or fog irrigation system. The irrigation system was calibrated to apply 0.1 ml methanol per rose plant. This process of application was repeated every eight days.

For laboratory tests or limited field trials, leaves were sprayed to wetness with a fine mist from a hand-pumped 710 milliliter capacity adjustable sprayer. Rates of application with this manual method of application for field plants generally were not calibrated. This manual spray method was used to test individual plants or leaves. For instance, in cotton, individual plants were assayed for leaf enlargement by measuring and marking leaf pairs of the same size and at similar positions on separate plants. One cotton leaf was treated with a 30% methanol solution by misting the leaf to wetness and the other was marked as the control and misted with water. Cotton leaves were treated with three applications and measured for median length and width after 20 days. As another example, individual green cabbage plants were sprayed with a gradient of methanol concentrations to determine toxicity levels.

Continuous long-term contact of plant tissues with solutions of methanol caused tissue damage at the point of contact. Repeated applications were made when turgidity subsided; treatments were usually spaced 1–2 weeks apart. Field treatments were initiated 2 hours after sunrise and were completed at least 4 hours prior to sunset.

Agriculture

Vegetable and cotton crops were planted in irrigated rows as outdoor commercial crops in Maricopa County, Arizona during 1991. Cotton population was approximately 100,000 plants per hectare. Seed for field crops were from the following sources:

Savoy cabbage (*Brassica oleracea capitata*), Savoy King, Sakata Seed America, Inc. Green cabbage (*Brassica oleracea capitata*), Head Start, Hybrid, Asgrow Seed Company Short staple cotton (*Gossypium hirsutum*), Deltapine 90, Delta & Pine Land Company Durum Wheat Reva (*Triticum durum*), Arizona Origin, Borden Pasta Group Barley (*Hordeum vulgare*), Arizona Origin, Salt River Seed and Soybean Company Genoa canning tomato (*Lycopersicon esculentum*), Northrup King.

Horticulture

In Spring, commercial greenhouses in Maricopa County, Arizona were stocked with 3000 hybrid tea roses (Rosa spp.) of the following varieties: Rotary Rose, Paul Harris, Miss All-American Beauty, Tropicana, Blue Girl, Angel Face, First Prize, Lowell Thomas, Tiffany, Mr. Lincoln, John F. Kennedy, Joseph's Coat, Peace, and Queen Elizabeth. Roses were cultured in 8–12 liter plastic containers for growth from bare root stock to bud and bloom. Potting medium was composed of 90% bark, 5% river sand, and 5% topsoil. Roses were provided with Osmocote 17-6-10 Plus Minors and low biuret urea (46-0-0). Greenhouses were constructed of clear plastic sheet and were illuminated and heated by direct sunlight. Treated plants were in one entire greenhouse. Controls were in identically constructed neighboring greenhouses. Controls were given water through the mist irrigation system when treated plants were given 10% minimal enhancement methanol medium supplemented with 1 part per thousand Pounce 3.2 EC (FMC Corp., Chicago, Ill.) pyrethroid insecticide to prevent aphid infestation.

Trees were treated by spraying stems or foliage with methanol. Included were lemon (*Citrus limon*), sour orange (*Citrus aurantium*), grapefruit (*Citrus paradisi*), *Eucalyptus microfica, Olea europaea, Phoenix canariensis, Washingtonia robusta, Pinus eldarica* and *Pinus halepensis*. To test the effects of nutrient supplementation on soil amendment, five grapefruit trees were left in nutrient deficient states from the previous year. These grapefruit trees were N, S and Fe deficient, showing symptoms of reduced fruit yield, discolored foliage and chlorosis. Three of these nutrient deficient grapefruit trees were treated with N, S and Fe supplemented methanol solutions by spray applications over the bark on main stems.

Container seed starts of wheat, barley and tomato were germinated in 72-well plastic tree flats with 90% bark, 5% river sand, 5% topsoil and fertilizer. Wheat was subject to direct sunlight and water stress by eliminating two consecutive irrigation cycles and then resuming normal irrigation cycles. Wheat was treated with 20% methanol soluble major and minor nutrients two days prior to water stress. At maturity, 50 seed heads including the rachis, seed and chaff were weighed and seeds per head counted each for control and treated plants.

Barley (*Hordeum vulgare*) was tested for effects of low light intensity by shading with 85% blockage mesh or exposure to direct sunlight. Barley plants were selected for similarity and were juxtaposed in order to replicate conditions for treated plants and their controls. Barley was cultured in 8 liter plastic containers, each plant spaced 5 cm (diam etc.) from the nearest plant to prevent self-shading. Six sets of barley were prepared: two for direct sunlight, two for shade, and two for shade with glutamic acid, sodium salt (1 g/L in minimal enhancement methanol medium). Half of the sets were left untreated as the control and the other sets were treated with test solutions. In a repeat of the test and to confirm that sodium was not responsible for growth responses, glycine (2 g/L) was substituted for glutamate. Barley plants were given three spray treatments with methanol solutions during the two week test period. Increased turgidity was determined by measuring the angles of pre-treatment and post-treatment positions of barley leaves with a protractor. The 0–180 degree baseline was aligned vertically with the main axis of the central stalk.

For confirmation of yield increases given a standardized glycine medium, plants were treated with 20% minimal enhancement methanol medium supplemented with 2 g/L glycine during the cool late winter from 1 March to 1 April. Test plants were treated three times under cloudy weather conditions. The following cultivars were treated: "Ichiban" eggplant, "Genoa" tomato and "Sequoia" strawberry. Plants were 5–10 cm tall at the start of weekly treatments. Harvest was undertaken by cutting the entire shoot at the base. Live weights of the shoots and individual leaves were recorded for controls and methanol-glycine treated plants.

For a general houseplant formulation, 0.1% glycine in 10% minimal enhancement methanol medium was supplemented with 0.5% disodium glycerophosphate pentahydrate and manually applied to foliage as a fine mist. The glycerophosphate solution was applied to *Chrysanthemum indicum, Dieffenbachia sequine, Syngonium podophyllum, Scindapsus aureus, Ficus elastica* and *Coleus blumei*. Plants were observed for increases in turgidity and signs of toxicity for two weeks under artificial illumination.

During autumn in open fields, 20% methanol was sprayed on foliage of plants with $C_4$ metabolism: corn (*Zea mays* cultivar Sweetie 82, Sun Seeds Co.), sorghum (*Sorghum vulgare*), Bermuda grass (*Cynodon dactylon*) and johnsongrass (*Sorghum halepense*). Two or more foliar applications were made one week apart and plants were observed for one month. Corn leaf lengths and number of cobs were measured on tagged methanol treated plants and matched controls in adjacent rows within a ten acre field.

Results

Plants showed rapid responses to methanol just below toxicity levels. Toxicity levels of methanol varied according to anatomical location of application and variety of plant. Generally, stems withstood the highest concentrations; 80–100% methanol was applied directly to trunk sections of pine (*Pinus eldarica* and *Pinus halepensis*), palm (*Phoenix canariensis* and *Washingtonia robusta*), eucalyptus (*Eucalyptus microfica*), lemon (*Citrus limon*), sour orange (*Citrus aurantium*), grapefruit (*Citrus paradisi*) and olive (*Olea europaea*) trees with no observable damage. When applied to *Pinus eldarica* stems that had been trimmed three months earlier, 90% methanol caused sap to run out of old wounds within 12 hours. Penetration through woody bark of the pine branch was immediate and translocation was clearly evident from the new sap emergent upstream from treatment with methanol. Germlings of *Washingtonia robusta* palms were sprayed with 50% minimal enhancement methanol medium once per month for six months and five whole shoots of untreated controls averaged 15 grams each while five treated palm shoots averaged 26 grams each. Responses to a gradient of methanol concentrations on tomato (*Lycopersicon esculentum*) showed increased damage to leaf margins from 20–40% methanol and no phytotoxicity at 10% methanol within 4–10 days. Under direct sunlight, gains in growth of tomato plants treated three times with 10% minimal enhancement methanol medium were visible over controls within two weeks of treatment, controls showing 9–10 internodes and treated tomato plants showing 12–16 internodes. Treated tomato plants had leaves and stems which were 25–50% greater in diameter than controls. Fruiting development on treated tomato plants commenced 5–10 days earlier than controls.

Foliar requirements for methanol differed widely, for example, 50% methanol was applied to palm and eucalyptus leaves, but eggplant was treated with 10% methanol. Significant differences in optimal methanol concentrations for foliage were observed at the varietal level, exemplified by savoy cabbage at 20% methanol and green cabbage at 50% methanol concentration in water. Foliar applications far below established toxicity levels necessitated repeated applications to elicit rapid growth responses similar to applications made near the toxicity levels. For example, at 20% methanol concentration, green cabbage required 3–6 repeated applications to show response similar to a single 50% methanol application. Untreated control cabbages were similar in size to cabbages treated with one application of 20% methanol, but cabbages treated repeatedly with 20% methanol or one time with 50% methanol grew to approximately twice the size of controls in four weeks. With foliar treatment under direct noon sunlight, increased turgidity was observed within two hours of treatment with methanol. Increased turgidity in treated plants was particularly evident between irrigation cycles and in the afternoon when control plants wilted under direct sunlight. Treated plants stood erect and vigorous during periods that controls were water stressed. Under high noon direct sunlight, for example, foliar application of 30% methanol on cotton resulted in increased leaf turgidity within 4 hours and approximately 15% increased growth in height over untreated controls within two weeks. During 1990, when 45°–50° C. weather was experienced, treated cotton plants remained turgid while the rest of the crop wilted at peak afternoon temperatures. In a 56 acre field treated twice 12 weeks prior to harvest of cotton, fruit matured approximately 2 weeks earlier than untreated fields. This early maturation allowed irrigation to be terminated 2 weeks early.

Savoy cabbages were treated under direct sunlight with 20% methanol. During a week when temperature maxima were above 40° C., treated savoy cabbages remained turgid while controls wilted. During the fall, savoy cabbages treated with a single application of methanol showed approximately 50% increase in vegetative growth over controls after 2 weeks with larger, thicker and more numerous leaves. Savoy cabbages treated with multiple applications of methanol showed chlorosis and stunted growth after the fifth application, therefore, nutrient supplemented solutions containing urea and chelated iron were utilized to sustain growth. Four weeks after three treatments with 20% minimal enhancement methanol medium, treated cabbages were as much as twice the size of controls. In a long-term test for sixty days and undergoing ten applications of 20% minimal enhancement methanol medium, 10 treated savoy cabbages averaged 3.5–4.0 kilograms per individual head while 10 controls averaged 2.0–2.5 kilograms per individual head. In a practical field test of rate of maturation, 100 savoy cabbage plants were treated five times during the fall season of 1991 with 20% minimal enhancement methanol medium. Harvest was undertaken by uninformed field hands who selected only those cabbage heads that were greater than 1–1.5 kilograms each. Treated savoy cabbages matured more evenly and earlier than 100 untreated controls. Of the 100 treated savoy cabbage plants, 75 heads were harvested on first pick. In contrast, 16 percent of the untreated savoy cabbage plants were harvested on first pick. Control rows of savoy cabbage were adjacent directly north, east, west or south of the treated cabbages. Largest heads were found in the treated areas weighing 3.5–4 kilograms. The largest heads found in control rows were 2.5–3.0 Kilograms.

Further cabbage assays were undertaken on winter sets during short days when cloud cover and rain was frequent. Under these cool, wet, low-light intensity conditions of winter, differences between treated and control cabbages were generally imperceptible.

All varieties of hybrid tea roses (Rosa spp.) including Rotary Rose, Paul Harris, Miss All-American Beauty, Tropicana, Blue Girl, Angel Face, First Prize, Lowell Thomas, Tiffany, Mr. Lincoln, John F. Kennedy, Joseph's Coat, Peace, and Queen Elizabeth were treated with weekly foliar applications of 10% minimal enhancement methanol medium plus 0.1% pyrethroid insecticide. Preliminary tests with high concentrations of iron showed that 0.9 gm/L FeHEEDTA in methanol was phytotoxic, but 0.08 gm/L in methanol was the maximum concentration tolerated by young rose foliage. A very high C:N ratio was achieved in the final foliar application since no urea was added to the third and last application. When treated with methanol, Rotary Rose, Paul Harris, Miss All-American Beauty, Blue Girl, Tiffany, Mr. Lincoln, John F. Kennedy, Joseph's Coat, Peace, Lowell Thomas and Queen Elizabeth grew to bud and bloom within 62 days of placement in the greenhouse. Treated Angel Face, First Prize and Tropicana required approximately 70 days to reach bud and bloom. In the control greenhouse, all varieties required 75–80 days to achieve bud and bloom maturity. Treated roses showed fuller foliage and blooms than controls. Individual flowers from treated Miss All-American Beauty, for example, showed average live weights of 26 grams each as compared to controls averaging 18 grams for each individual bloom. At the time of first blooms opening, treated Paul Harris plants averaged 8 fully opened flowers. Controls later averaged 4 fully opened flowers upon first break of open flowers. Plants remained healthy and pest-free.

Durum wheat (*Triticum durum*) was treated weekly under direct sunlight with three applications of 20% methanol with soluble major and minor nutrients prior to water stress. After elimination of the second irrigation cycle, controls wilted for approximately two hours each afternoon, but methanol treated plants stood erect and turgid. Treated wheat foliage averaged more than 50% greater in length and 35% greater in width than blades of untreated controls 45 days after planting. At harvest, treated wheat averaged 18 plump seeds per culm and controls averaged 12 small seeds per culm. Individual dry seed heads averaged 0.36 gm from treated plants and 0.16 gm from controls.

Methanol was applied to short staple cotton (*Gossypium hirsutum*) planted out-of-doors in irrigated rows from June through August. Within two weeks of treatment with 30% minimal enhancement methanol medium, cotton plants showed greater turgidity and had larger leaves than controls. Treatment with methanol stimulated production of cotton leaves to 20–100% greater surface area and approximately 25–50% greater thickness over controls in two to three weeks. Greatest leaf increase was observed in the upper canopy and least improvement was observed in lowest leaves. Individual cotton plants received approximately 0.5 ml methanol per plant by tractor spray apparatus. Treated cotton plants required irrigation repetitions 9 days apart when control plants required 7 day irrigation cycles during a 20–30 day period following methanol application.

In parallel tests on individually marked cotton leaves on separate plants that were fully exposed to direct sunlight, 10 leaves were sprayed with 30% methanol and 10 controls were sprayed with water. Only 6 paired leaves remained for final measurement at termination of 20 days due to loss of identification tags or leaf damage. Treated plants showed consistent leaf enlargement of at least 20% in length and width over controls. Individual dried leaves of treated plants averaged approximately 2.5–3.5 grams and individual control leaves averaged approximately 1.2–2.5 grams.

Correction of nutrient deficiency in citrus was made by application of a 10-fold concentrate methanol soluble major and minor nutrient enhancement medium. At three month intervals, the 100% methanol nutrient concentrate was sprayed on the trunks of three nutrient deficient grapefruit (*Citrus paradisi*) trees. At the beginning of the new growth season, no foliar symptoms of nutrient deficiency were observed in new foliage of treated trees, but controls which received no treatment continued to produce foliage showing yellow-veined symptoms of nutrient deficiencies.

After two weeks under direct sunlight conditions, barley treated with minimal enhancement methanol medium showed approximately 50% increase in vegetative growth over controls. Under subdued light, controls were slightly etiolated and averaged 10.5 cm in height. Barley treated with minimal enhancement methanol medium under low light averaged 6.3 cm in height and had wilted brown leaf tips. With the addition of glutamate to minimal enhancement methanol medium, barley plants averaged 12.3 cm height under low light conditions. In the repeat of the test with glycine substituted for glutamate, barley plants showed similar improvement of growth in the shade. Barley plants that were treated with glycine and methanol showed turgidity increases within 30 minutes under direct sunlight and after several hours in the shade. Wilted blades of treated plants rose 25 degrees in angle above their pre-treatment position when under direct sunlight.

The detoxifying characteristics of glycine observed in tests with shaded barley implied that higher concentrations of methanol could be applied without injury. With the addition of glycine to methanol solutions, rose and tomato showed no phytotoxicity from 20% methanol solutions. Without glycine, rose and tomato plants developed brittle brown leaf margins after treatment with 20% methanol. Treatments of plants with methanol-glycine solutions followed by placement of plants under very low light intensity indoors resulted in formation of irregular dark areas corresponding to areas of accumulation of the treatment solution on leaf surfaces after 48 hours.

Based on our observation that the addition of glycine improved plant response under shaded sunlight and that glycine reduced toxicity of methanol, a standard solution for use during cloudy weather or with indirect sunlight was formulated as follows: 20% methanol, 0.1% urea, 0.1% urea phosphate, 0.1% glycine, 0.05% Triton X-100 and water. This standard formulation was applied manually once per week for 3 weeks to eggplant, strawberry and tomato plants cultured in containers out-of-doors with the following improvements of yield as compared with controls (Table 1).

TABLE 1

| Plant Name | Entire Plant Yield (g) | | Total Leaf Number (Largest Individual Leaf (g)) | |
|---|---|---|---|---|
| | Treated | Control | Treated | Control |
| Eggplant | 57 | 35 | 17 (5.6) | 7 (4.4) |
| Strawberry | 28 | 17 | 7 (4.1) | 5 (2.6) |
| Tomato | 65 | 41 | | |

After treatment with methanol-glycine formulations, plants required exposure to sunlight prior to development of irregularly-shaped black areas on foliage. No foliar damage was observed when plants were exposed to sunlight within 24 hours of methanol-glycine treatments. Based on the post-treatment requirement for photosynthesis to detoxify glycine supplementation, glycerophosphate was added. A 20% methanol+glycine+glycerophosphate solution was applied to rose plants indoors with methanol-glycine, methanol and water-misted controls. After 5 days, the water-misted controls were slightly etiolated showing elongate internodes, and the control rose plants showed water stress, all flowers wilted; methanol controls showed extensive phytotoxicity effects with brittle dead brown whole leaves and leaf portions; methanol-glycine controls showed irregular black areas on leaves; methanol+glycine+glycerophosphate treated rose bushes were healthy, green, and turgid with blooms erect and developing to fullness.

Under fluorescent lights (75–100 µEin/m$^2$/sec), increased turgidity of subapical leaves of *Ficus elastica* was evident within 2 hours of treatment with the methanol+glycine+glycerophosphate solution, leaves rising 45–60 degrees vertically from initial horizontal positions. Similarly, with foliar applications of 20% methanol+glycine+glycerophosphate, *Chrysanthemum indicum*, *Dieffenbachia sequine*, *Syngonium podophyllum* and *Scindapsus aureus* showed increased turgidity and healthful growth indoors with artificial illumination over a period of one week. Daily treatments of *Coleus blumei* with 20% methanol+glycine+glycerophosphate resulted in plants with average individual weights of 43 grams as compared to water-misted controls with average individual weights of 36 grams after one week.

No positive growth effects were observed after application of any concentration of methanol to plants with $C_4$ metabolism: corn, sorghum, Bermuda grass or johnsongrass. In general, five foliar applications of 20% methanol caused minor leaf damage and no greater leaf expansion or early maturation than controls. Methanol treated corn showed no differences in fruit or vegetative measurements when compared to controls. Foliage of corn plants treated repeatedly with methanol showed linear brown areas along median leaf veins and undulating leaf texture as compared with normal flat surfaces on controls.

Yield improvements from the various plants tested are summarized in Table 2.

TABLE 2

| | Summary of Yield Improvements | |
|---|---|---|
| Plant | Weight improvement over control | Period of treatment (days) |
| Tomato | 50% | 30 |
| Strawberry | 60% | 30 |
| Eggplant | 60% | 30 |
| Cotton | 50% | 30 |

TABLE 2-continued

Summary of Yield Improvements

| Plant | Weight improvement over control | Period of treatment (days) |
|---|---|---|
| Savoy cabbage | 50% | 60 |
| Wheat (fruit yield) | 100% | 60 |
| Rose | 40% | 45 |
| Palm | 70% | 180 |

Amino acid treatment is best undertaken in combination with a low concentration (1–10 mM) of an available source of phosphate such as glycerophosphate, trimethyl phosphate, etc. Optimal dosages place 0.01–0.1 gm amino acid per square foot of leaf surface area during lengthy periods of photorespiratory stress. For example, cotton was treated with a Growth Improvement Glycerophosphate-Amino acid (GIGA) solution containing: 0.5% glycine; 0.2% glycerophosphate, calcium salt; 0.02% Triton X-100; and water. The solution was adjusted to pH 6.5 with citrate-phosphate buffer. At onset of third pinhead square, the foliage of each plant was treated by backpack sprayer with 5 ml of the solution per plant once per week for three weeks. Six controls were tested including: untreated water, surfactant, glycine and surfactant, glycerophosphate and surfactant, and 20% methanol+surfactant. Cotton plants were cultured in plastic containers under greenhouse conditions similar to those previously described for rose studies. The highest afternoon light intensity reached approximately 800–1000 µEin/m$^2$/sec and untreated control plants normally wilted 4 to 6 hours per day as temperatures rose above 100° F. The surface area of three leaves per plant were measured 30 days after the initial treatment and the dry weights of the leaves were determined. Statistical analyses of results indicated direct correlation of dry weight to leaf surface area with the probability of sameness at unity. The GIGA and 20% methanol and surfactant solutions showed significant increases of leaf surface area over other controls. Inferential analysis with paired sample T-test on GIGA vs. 20% methanol and surfactant test populations with 16 cases showed mean difference=5.648, Standard Deviation difference= 15.417, T=1.465, Degrees of Freedom=15, and probability= 0.164. The GIGA treated population averaged larger leaves (mean=79 cm$^2$) as compared to the methanol treated population (mean=73 cm$^2$). The average leaf surface area of all other test populations (62 cm$^2$) was approximately 25% smaller than GIGA treated cotton. For example, a paired samples T-test on GIGA group vs. Water control group showed mean=19.861, SD=16.867, T=4.710, DF=15, and probability=0.000. The very low value for probability of sameness between the GIGA and Water treated groups indicates significant difference in populations. Statistical analysis also indicates that the combination of a phosphate source and glycine is necessary for growth improvement as paired samples T-test on GIGA vs. glycine and surfactant yields mean=15.233 and probability=0.006 and T-test on GIGA vs. glycerophosphate and surfactant yields mean= 18.031 and probability=0.009. Inferential analysis clearly indicates that of all the groups studied, GIGA treatments showed greatest growth of foliage.

Although the foregoing invention has been described in detail for purposes of clarity of understanding, it will be obvious that certain modifications may be practiced within the scope of the appended claims.

What is claimed is:

1. A method for promoting growth in plants, said method comprising:

applying a growth promoting composition to the plant as a foliar spray, wherein said growth promoting composition contains (a) an amount of methanol or methanol metabolite selected from the group consisting of formaldehyde, formic acid, and methyl formate sufficient to increase plant turgidity and enhance carbon fixation within the plant, wherein said amount is at at least 10% by volume, and (b) an amount of an agriculturally acceptable surfactant effective to enhance wetting of the plant and penetration of methanol into the plant; and exposing the plants to a minimum light intensity of 1000 µEin/m$^2$/sec for a period of at least two hours after application of the growth promoting composition.

2. A method as in claim 1, wherein the plant is a higher plant which fixes carbon dioxide by the $C_3$ pathway.

3. A method as in claim 1, wherein the foliar spray is applied in the direction of the incident radiation or on all leaf surfaces including underside.

4. A method as in claim 1, wherein the growth promoting composition contains methanol at a concentration from 10% to 50% by volume.

5. A method as in claim 1, wherein the growth promoting composition further comprises glycine.

6. A method as in claim 1, wherein the growth promoting composition further comprises an α-glycerophosphate.

7. A plant growth promoting composition comprising an aqueous solution of methanol or methanol metabolite selected from the group consisting of formaldehyde, formic acid, and methyl formate present in an amount sufficient to increase plant turgidity and enhance carbon fixation when applied to a plant, wherein the methanol is present at least 10% by volume, said solution further comprising a nitrogen nutrient source and a phosphorus nutrient source present in amounts sufficient to provide said nutrients to a treated plant and an amount of agriculturally acceptable surfactant effective to enhance surface wetting and methanol penetration in a treated plant, wherein the nitrogen source is selected from the group consisting of urea, urea formaldehyde, isobutylidene urea, sulfur coated urea, nitrates, nitrate of soda, calcium nitrate, ammonium salts, and an amino acid selected from the group consisting of glycine, glutamate, glutamine, alanine, and aspartate, and the phosphorus source is selected from the group consisting of phosphate salts, phosphate salts and phosphate esters of carbohydrate metabolites, organophosphates, pyrophosphates, polyphosphates, concentrated superphosphates, nitric phosphates, urea phosphate, monocalcium phosphate, francolite, orthophosphoric acid, and trimethyl phosphate.

8. A plant growth promoting composition as in claim 7, wherein the aqueous solution contains methanol present at from 10% to 50% by volume.

9. A plant growth promoting composition as in claim 7, further comprising an iron nutrient source present in an amount sufficient to provide said nutrient to a treated plant.

10. A plant growth promoting composition comprising an aqueous solution of from 5% to 50% by volume methanol, 0.1 g/l to 5 g/l glycine, and an agriculturally acceptable surfactant.

11. A plant growth promoting composition as in claim 10, further comprising a nitrogen nutrient source, a phosphorus nutrient source, and an iron nutrient source.

12. A plant growth promoting composition as in claim 11, wherein the nitrogen nutrient source is selected from the group consisting of urea, urea formaldehyde, isobutylidene urea, sulfur-coated urea, nitrates, nitrate of soda, calcium nitrate, ammonium salts, and an amino acid selected from the group consisting of glycine, glutamate, glutamine, alanine, and aspartate, the phosphorus nutrient source is selected from the group consisting of phosphate salts, phosphate salts and phosphate esters of carbohydrate metabolites, organophosphates, pyrophosphates, polyphosphates, concentrated superphosphates, nitric phosphates, urea phosphate, monocalcium phosphate, francolite, orthophosphoric acid, and trimethyl phosphate and the iron source is selected from the group consisting of EDTA-chelated iron, versenes-chelated iron; HEEDTA, NTA, DTPA, or EDDHA-chelated iron; nitrilotriacetic acid-chelated iron; acetate-chelated iron; humate-chelated iron; iron filings; iron sulfate; iron oxalate; and ferric chloride.

13. A plant growth promoting composition as in claim 10, further comprising a glycerophosphate present at a concentration from 0.1 g/l to 10 g/l.

* * * * *